(12) United States Patent
Boehlke

(10) Patent No.: US 8,109,945 B2
(45) Date of Patent: Feb. 7, 2012

(54) PERCUTANEOUS SUTURE PATH TRACKING DEVICE WITH CUTTING BLADE

(75) Inventor: Raimar Boehlke, Excelsior, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1763 days.

(21) Appl. No.: 11/051,892

(22) Filed: Feb. 4, 2005

(65) Prior Publication Data

US 2006/0178682 A1  Aug. 10, 2006

(51) Int. Cl.
*A61B 17/04* (2006.01)

(52) U.S. Cl. ......................................................... 606/148

(58) Field of Classification Search .................. 606/139, 606/144, 148, 145, 167, 170, 138
See application file for complete search history.

(56) References Cited

U.S. PATENT DOCUMENTS

| | | | |
|---|---|---|---|
| 4,317,445 A | 3/1982 | Robinson | |
| 4,602,635 A | 7/1986 | Mulhollan et al. | 128/334 R |
| 5,192,302 A | 3/1993 | Kensey et al. | 606/213 |
| 5,222,974 A | 6/1993 | Kensey et al. | |
| 5,242,456 A | 9/1993 | Nash et al. | 606/142 |
| 5,242,459 A * | 9/1993 | Buelna | 606/148 |
| 5,292,327 A | 3/1994 | Dodd | 606/148 |
| 5,304,184 A | 4/1994 | Hathaway et al. | 606/148 |
| 5,324,298 A | 6/1994 | Phillips et al. | 606/148 |
| 5,397,326 A | 3/1995 | Mangum | 606/148 |
| 5,403,329 A | 4/1995 | Hinchcliffe | 606/147 |
| 5,405,354 A | 4/1995 | Sarrett | |
| 5,411,520 A | 5/1995 | Nash et al. | 606/213 |
| 5,417,699 A | 5/1995 | Klein et al. | 606/144 |
| 5,423,837 A | 6/1995 | Mericle et al. | 606/148 |
| 5,431,666 A | 7/1995 | Sauer et al. | 606/139 |
| 5,454,821 A | 10/1995 | Harm et al. | 606/148 |
| 5,462,561 A | 10/1995 | Voda | 606/144 |
| 5,549,618 A | 8/1996 | Fleenor et al. | 606/148 |
| 5,584,861 A | 12/1996 | Swain et al. | 606/232 |
| 5,613,974 A | 3/1997 | Andreas | 606/144 |
| 5,653,719 A | 8/1997 | Raiken | 606/148 |
| 5,662,681 A | 9/1997 | Nash et al. | |
| 5,746,755 A | 5/1998 | Wood et al. | |
| 5,766,183 A | 6/1998 | Sauer | 606/139 |
| 5,769,862 A | 6/1998 | Kammerer et al. | 606/148 |
| 5,782,861 A | 7/1998 | Cragg et al. | 606/216 |
| 5,797,929 A | 8/1998 | Andreas et al. | 606/148 |
| 5,855,585 A | 1/1999 | Kontos | 606/144 |
| 5,910,155 A | 6/1999 | Ratcliff et al. | 606/213 |
| 5,997,555 A | 12/1999 | Kontos | |
| 6,007,563 A | 12/1999 | Nash et al. | 606/216 |
| 6,024,747 A | 2/2000 | Kontos | 606/144 |
| 6,042,601 A | 3/2000 | Smith | |
| 6,117,144 A | 9/2000 | Nobles et al. | |
| 6,132,439 A | 10/2000 | Kontos | 606/139 |
| 6,183,485 B1 | 2/2001 | Thomason et al. | 606/148 |
| 6,245,080 B1 | 6/2001 | Levinson | 606/144 |
| 2003/0181926 A1 * | 9/2003 | Dana et al. | 606/148 |
| 2004/0254598 A1 * | 12/2004 | Schumacher et al. | 606/170 |
| 2007/0173865 A1 * | 7/2007 | Oren et al. | 606/148 |

* cited by examiner

*Primary Examiner* — Amy Lang

(74) *Attorney, Agent, or Firm* — Holland & Hart

(57) ABSTRACT

The present invention is directed to methods and apparatus for cutting filaments percutaneously. The methods and systems may be used in conjunction with sealing a puncture percutaneously in tissue separating two internal portions of the body of a living being with an anchor, a sealing plug and a filament connecting the anchor and sealing plug. The present invention provides for safe filament cutting below the skin and may reduce the risk of cutting the filament distal of any knots.

26 Claims, 10 Drawing Sheets

PERCUTANEOUS SUTURE PATH TRACKING DEVICE WITH CUTTING BLADE

FIELD OF THE INVENTION

This invention relates generally to medical devices and more particularly to devices for cutting sutures or other filaments percutaneously.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,963; 6,090,130; and 6,045,569 and related patents that are hereby incorporated by reference.

Typical closure devices such as the ones described in the above-mentioned patents sandwich the puncture site with an internal anchor and an external sealing plug. The internal anchor and external sealing plug are attached by a suture. The suture is typically slip-knotted proximal of the sealing plug to cinch and hold the sealing plug adjacent to the anchor. A tamping tube is often used to force the sealing plug toward the anchor. Even after tamping the sealing plug and cinching the suture, the suture extends from the puncture and through the skin. It is desirable, however, to cut the suture percutaneously to promote healing.

Consequently, an operator usually pulls the suture, stretching the suture a certain length outside of the incision. The suture is then cut as close as possible to the base of the incision, which releases the pulling pressure and usually springs the suture back within the incision below the outside skin level. Thus, the suture is typically not exposed from the incision after it is cut. However, there is a risk of pulling too hard on the suture and compromising the seal of the anchor and the sealing plug. In addition, the small amount of stretch available by pulling the suture usually leaves the end of the suture very close to, or even protruding slightly from, the surface of the skin. Therefore, there is a need for cutting sutures percutaneously without excessive pulling on the suture, such that the sutures are cut well below the skin surface.

SUMMARY

The present invention meets the above-described needs and others. Specifically, the present invention provides methods and systems for cutting filaments percutaneously. However, unlike prior systems, the present invention provides for safe filament cutting below the skin surface while reducing the risk of cutting the filament distal of any knots. The present invention may be used in connection with a tissue puncture closure device following sealing of a puncture.

In one of many possible embodiments, the present invention provides a percutaneous filament cutting device. The percutaneous filament cutting device comprises a housing, an elongated cutter guide attached to and extending from the housing, and an elongated cutter slidingly disposed in the housing and extending partially through the elongated cutter guide. A biasing member may be disposed between the elongated cutter and the housing for biasing the elongated cutter to a first position. The elongated cutter may comprise an actuator tab extending through a hole in the housing for operating the elongated cutter. The elongated cutter may comprise a blade end and an actuator end, the actuator end having a tab extending outside of the housing.

According to some aspects of the invention, a distal end of the elongated cutter guide may include a filament insertion slot. The filament insertion slot may be helical, and the distal end of the elongated cutter may also include a longitudinal guide slot open to the helical filament insertion slot. The helical filament insertion slot and the longitudinal guide slot may form an acute angle. The filament insertion slot may include a one-way door movable radially inward but not movable radially outward for caging a filament. the one-way door may comprise a cantilevered arm having a detent hinge According to some aspect of the invention, a molded tip may be coupled to the elongated cutter guide, and the molded tip may have a filament insertion slot and the one-way movable door. The molded tip includes a tapered outer distal end abutting and flush with the elongated cutter guide, a radially inward taper receptive of the filament and leading to an internal filament lumen, the internal filament lumen having a diameter no more than three times a diameter of an associated filament. The internal filament lumen may comprise a diameter of no more than approximately 0.35 mm.

According to some embodiments of the percutaneous cutting device, the elongated cutter is coaxial with the elongated cutter guide. The elongated cutter and the elongated cutter guide may comprise hollow tubes.

Another aspect of the invention provides a suture path tracking and cutting device. The device comprises a handle, a shaft extending from the handle, the shaft having a first end and comprising a cutting window and a first suture insertion slot at the first end, a cutting blade disposed in the shaft and biased to a first position, and a tip attached to the shaft at the first end. The tip has a second suture insertion slot substantially aligned with the first suture insertion slot. The tip further comprises a one-way door for caging a suture.

According to some embodiments, the cutting window meets the first insertion slot at an open area. The cutting window extends distally from the open area and comprises a suture guide slot to prevent inadvertent release of the suture from the cutting window back through the first insertion slot. The cutting window may be shaped like a capsule and open at a side thereof to the first insertion slot. The first suture insertion slot may include a helical cut in the shaft. The helical cut may extend approximately 180° through the shaft.

According to some embodiments, the one-way door comprises a cantilevered arm extending across the second insertion slot in a first position, the one-way door moveable radially inward from the first position but not radially outward from the first position. The one-way door may comprise a compliant arm having a base, inside surface, an outside surface, a detent at the base of the outside surface, and a protrusion at the base of the inside surface. The shaft and tip may define a lumen receptive of a suture with an effective diameter comprising no more than approximately three times the diameter of the suture. Therefore, the lumen may be sized to receive one diameter of the suture, but not allow any knots in the suture to pass therethrough.

According to some embodiments of the suture path tracking and cutting device, the cutting blade is disposed in the shaft proximal of the cutting window in the first position, the cutting blade being movable distally at least partially across the cutting window in response to a force applied thereto. An actuator tab connected to the cutting blade may be used for moving the cutting blade within the shaft, the actuator tab extending outside of the handle.

Another aspect of the invention provides a method of cutting a suture percutaneously. The method includes providing a housing, providing an elongated cutter guide attached to and extending from the housing, providing an elongated cutter slidingly disposed in the housing and extending partially through the elongated cutter guide, inserting the suture into the elongated cutter guide, passing a tip of the elongated cutter guide below surface skin level, and actuating the elongated cutter. The method may also include blocking any knots tied in the suture from entering the elongated cutter guide and/or preventing release of the suture from the cutter guide with a one-way door.

According to some aspects of the method, the actuating comprises depressing a tab of the elongated cutter against a biasing force. In addition, the inserting may comprise threading the suture through a guide slot in the elongated cutter guide, and the actuating may comprise sliding the elongated cutter past the window to sever the suture.

Another aspect of the invention provides another method of cutting a filament percutaneously. This method comprises threading a filament extending from an incision in a patient through a cutter guide, preventing release of the filament from the cutter guide, following the filament path into the incision with the cutter guide, sliding a blade through the cutter guide, and severing the filament with the blade. The threading may comprise passing a portion of the filament through an insertion slot in the cutter guide and into a guide slot. The sliding may comprise depressing a tab operatively connected to the blade.

Another embodiment of the invention provides an internal tissue puncture closure and cutting system. The system comprises a closure device and a filament cutting device insertable percutaneously into an incision for cutting the filament below a skin level. The closure device comprises a filament extending from a first end of the closure device to a second end of the closure device, an anchor for insertion through the tissue wall puncture attached to the filament at the second end of the closure device, a sealing plug slidingly attached to the filament adjacent to the anchor, a driving mechanism for tamping the sealing plug toward the second end, and a filament cutting device insertable percutaneously into an incision for cutting the filament below a skin level.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1:
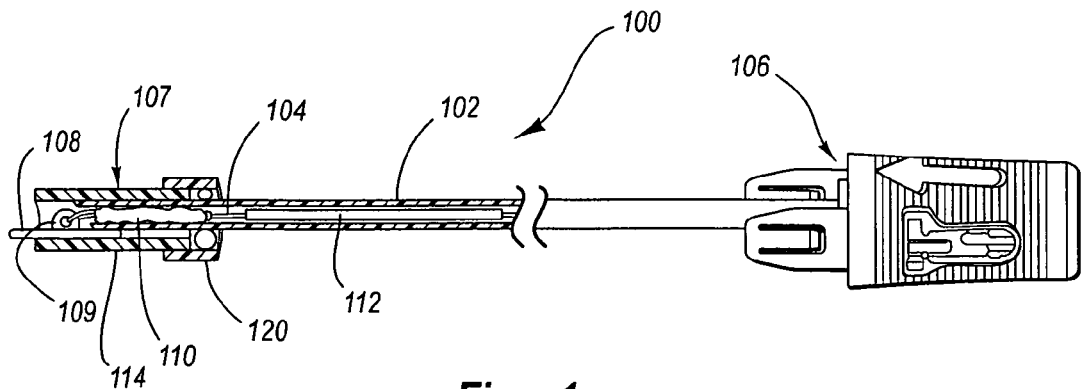
FIG. 1 is a partial cut-away view of a tissue closure device according to the prior art.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, after sandwiching the puncture, a filament usually extends from the sealing plug and out through the incision. The filament must be cut to release the sealing plug and anchor from the remainder of the closure device. It is difficult to cut the filament percutaneously with conventional tools such as scissors, and therefore the filament often protrudes out of the skin. The present invention describes methods and apparatus to seal tissue punctures and/or cut filaments percutaneously. The percutaneous filament cutting devices of the present invention may be particularly useful for use with tissue puncture closure devices. Some specific tissue puncture closure devices are shown. However, the cutting devices may be used with any tissue puncture closure device, and also in other environments in which is desirable to cut a filament below a surface level. The principles described herein may be used with any vascular closure device or other circumstances requiring subsurface filament cutting. Therefore, while the description below is directed primarily to arterial procedures and certain embodiments of a vascular closure device, the methods and apparatus are only limited by the appended claims.

As used in this specification and the appended claims, the term "tamp" or "tamping" is used broadly to mean packing down by one or a succession of blows or taps, but not by excessive force. A "lumen" refers to any open space or cavity in a bodily organ or in a tool. The term "percutaneous" means passed, done, or effected through or under the skin surface or other subsurface structure. A "tab" is a projection, flap, or short strip attached to or integral with an object to facilitate operation. An "effective diameter" is a smallest distance across a closed or generally closed shape, and is not necessarily circular. The words "including" and "having," as used in the specification, including the claims, have the same meaning as the word "comprising."

Referring now to the drawings, and in particular to FIGS. 1-5, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4). The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
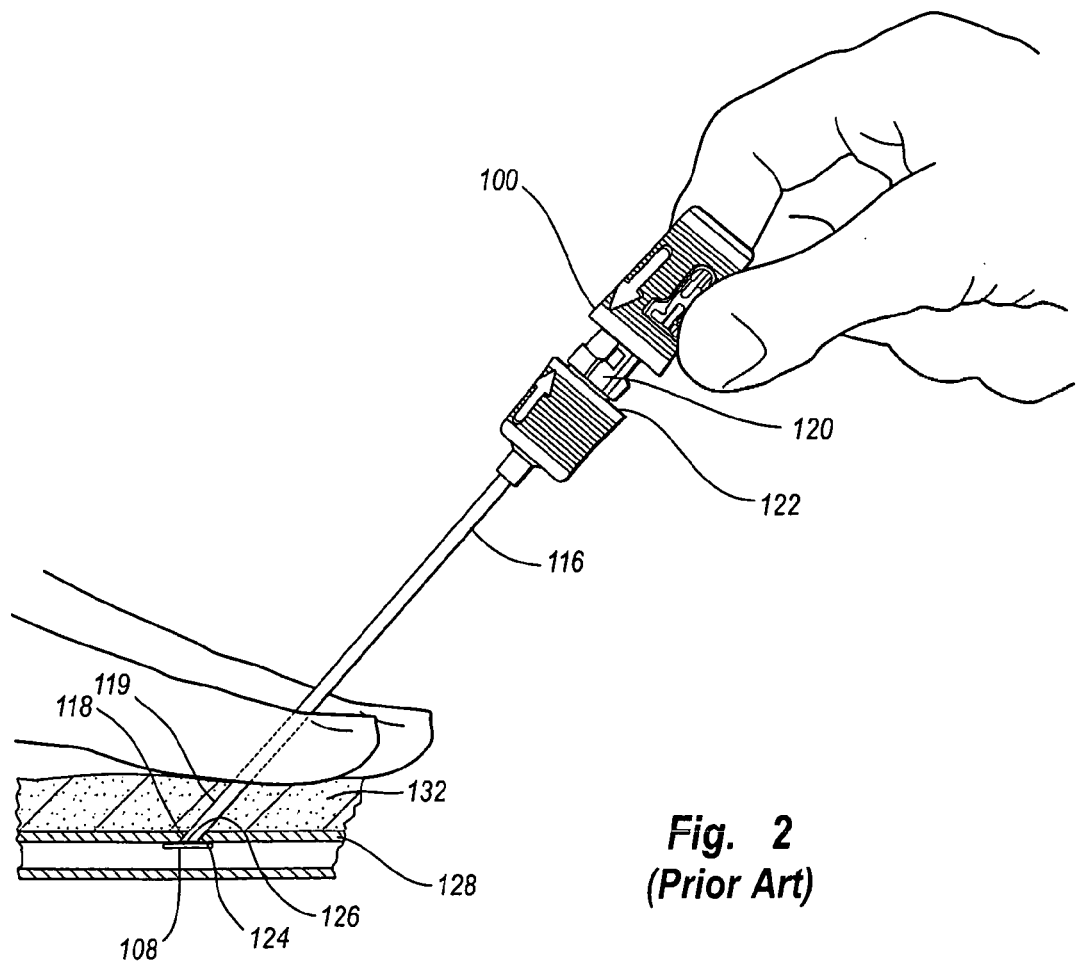
FIG. 2 is a side view of the tissue closure device of FIG. 1 engaged with an artery according to the prior art.
Figure 3:
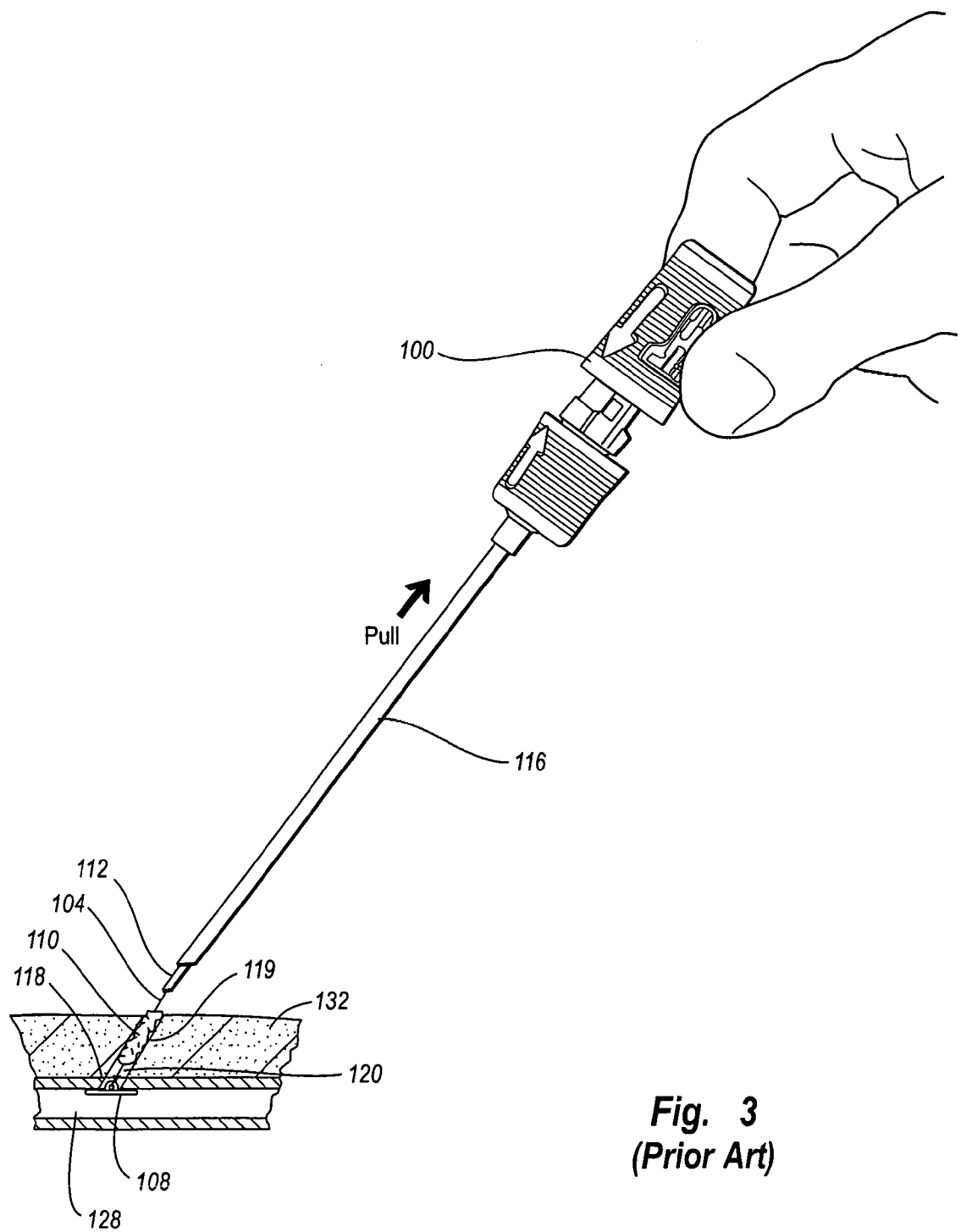
FIG. 3 is a side view of the tissue closure device of FIG. 1 being withdrawn from an artery according to the prior art to deploy a collagen sponge.
Figure 4:
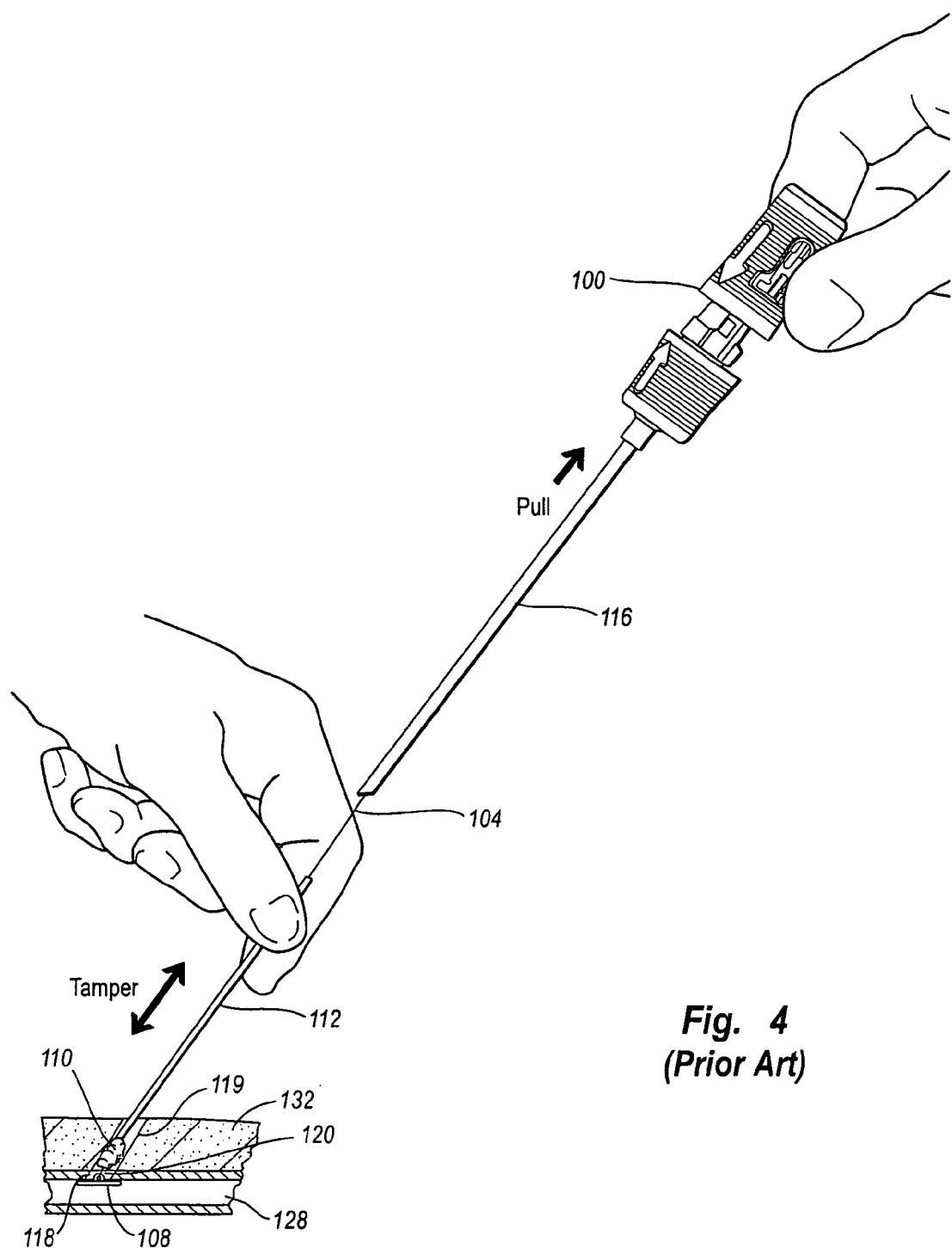
FIG. 4 is a side view of the tissue closure device of FIG. 1 illustrating tamping of the collagen sponge according to the prior art.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, depositing the collagen pad 110 in the incision tract 119 and exposing the tamping tube 112. With the tamping tube 112 fully exposed as shown in FIG. 4, the collagen pad 110 is manually tamped, and the anchor 108 and collagen pad 110 are cinched together and held in place with the self-tightening slip-knot on the suture 104. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, the tamping of the collagen pad 110 commences after sheath 116 has been removed so as to expose the tamping tube 112 for manual grasping. However, automatic tamping or other driving mechanisms may also be used to tamp the collagen pad 110 according to principles of the present invention.

Figure 5:
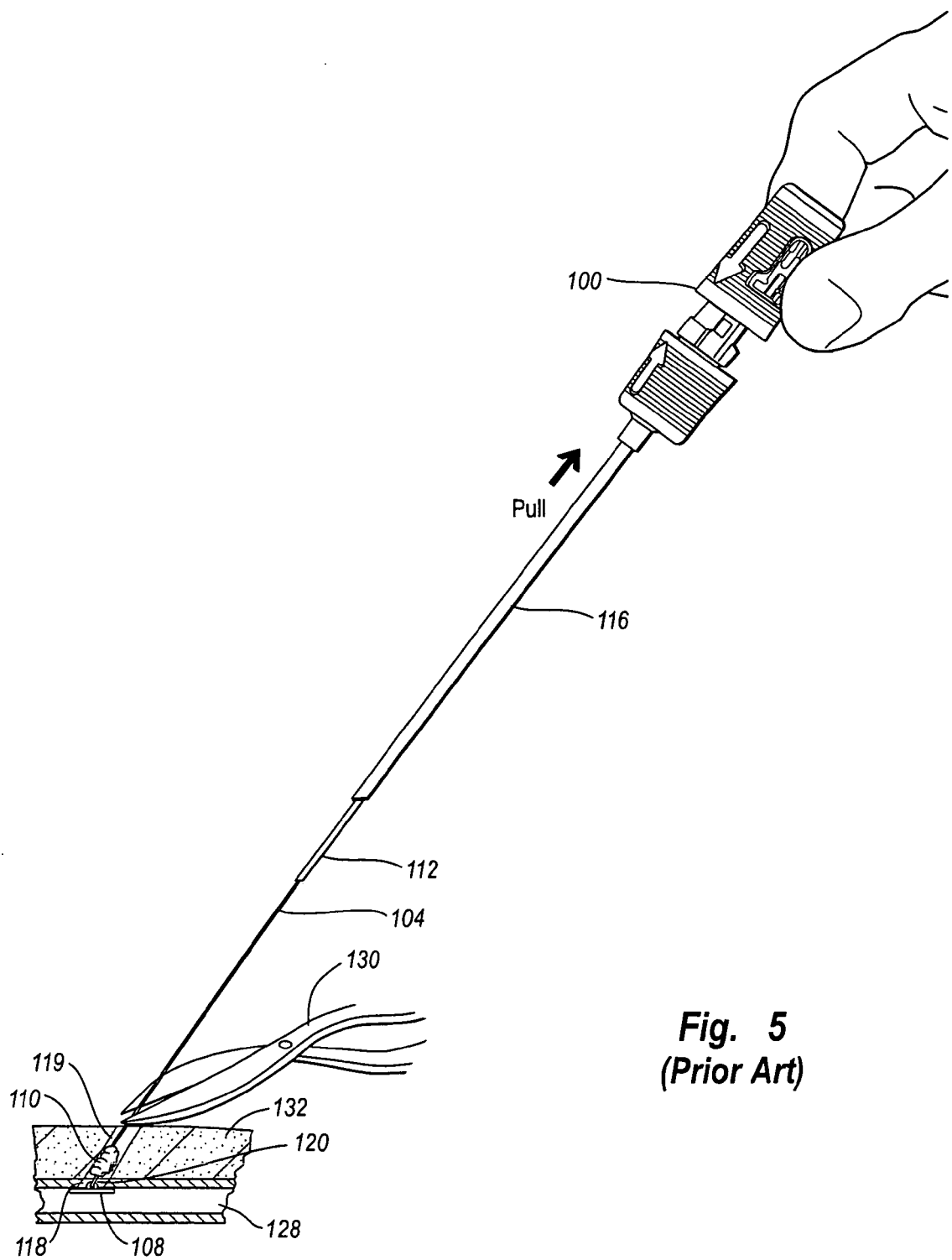
FIG. 5 is a side view of the tissue closure device of FIG. 1 illustrating a suture being cut according to the prior art.

As shown in FIG. 5, when the collagen pad 110 has been tamped and cinched, the suture 104 connecting the anchor 108 and the pad 110 must be cut proximal of the pad 110 to release the closure device. Typically a pair of scissors 130 is used to cut the suture 104 as close as possible to the surface of a skin layer 132. The suture 104 may even be stretched so that after the cut, the suture 104 recoils slightly below the surface of the skin layer 132. Nevertheless, the suture 104 typically protrudes slightly from the skin layer 132 or is very close to the surface of the skin layer 132, which can cause irritation or other problems to a patient.

Therefore, the present specification describes a percutaneous cutting device or suture path tracking and cutting device that enables cutting filaments safely below a skin or other surface. The filament is preferably threadable through the cutting device at any point along the filament and able to slide along the filament to a desired cutting position.

Figure 6:
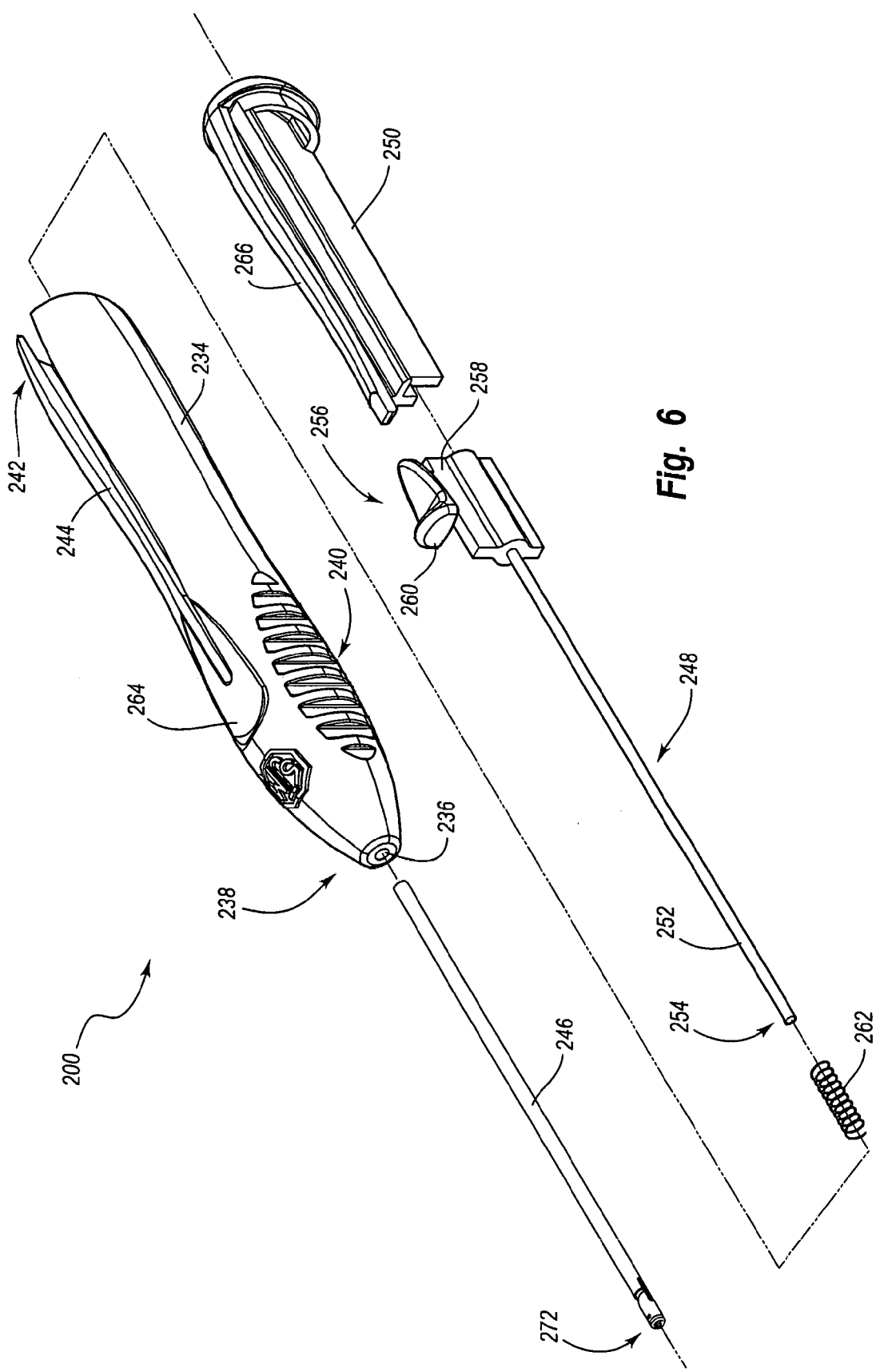
FIG. 6 is an exploded view of a percutaneous filament cutting device according to one embodiment of the present invention.

Referring now to FIG. 6, a suture path tracking and cutting device, such as a percutaneous cutting device 200, is shown according to one embodiment of the present invention. The percutaneous cutting device 200 may have particular utility when used in connection with tissue puncture closure devices such as the closure device 100 described above. However, any subsurface filament cutting operation may be accomplished with the percutaneous cutting device 200.

The percutaneous cutting device 200 includes a handle 234 housing or partially housing a number of other components. The handle 234 is preferably plastic with an ergonomic shape for comfortable manipulation by an operator. As shown in FIG. 6, the handle 234 is elongated and tapers to an opening 236 at a first end 238. The handle 234 may also include a first set of gripping detents 240 and a second similar or identical set on an opposite side. The handle 234 may be open at a second end 242 and have a hole or slit 244 shown in FIG. 6 extending longitudinally.

The opening 236 of the handle 234 is receptive of an elongated cutter guide 246. The elongated cutter guide 246 may comprise a hollow tube which is attached to and extends from the handle 234 when the percutaneous cutting device 200 (FIGS. 7-8) is assembled. The second end 242 of the handle 234 is receptive of an elongated cutter 248 and an end cap 250. The elongated cutter 248 may comprise a second hollow tube 252 with a sharpened edge or cutting blade at a first or blade end 254. A second or actuator end 256 of the elongated cutter 248 is shown with a mount 258 attached to an actuating tab 260. A biasing member such as a spring 262 may be disposed between the handle 234 and the mount 258 of the elongated cutter 248 to bias the elongated cutter 248 to the first position.

Figure 7:
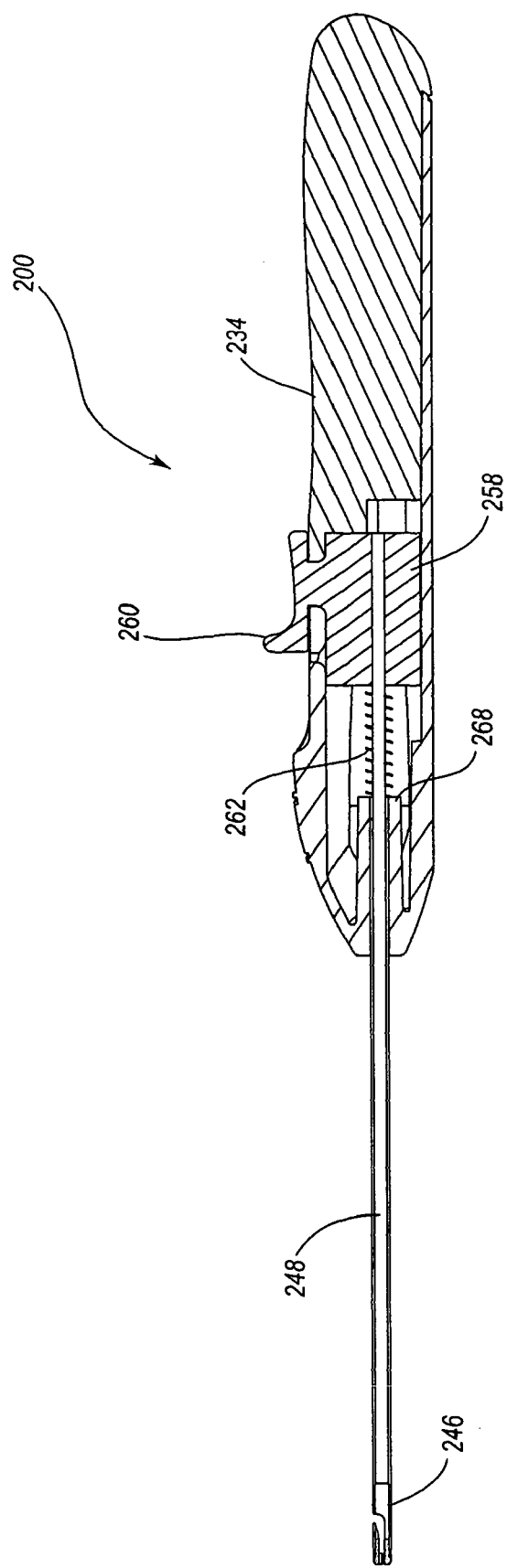
FIG. 7 is an assembled cross-sectional view of the percutaneous filament cutting device of FIG. 6.

The elongated cutter 248 slides into the handle 234 with the tab 260 extending outside of the handle 234 at a flattened surface 264 of the handle, when assembled (FIG. 7). The end cap 250 includes a track 266 that mates with the slot 244 of handle 234 to close the handle, although a portion or the slot 244 remains open for the tab 234 to extend through. Thus, the elongated cutter 248 is inserted into the handle 234 such that the mount 258 and the tab 260 straddle the slot 244. The tab 260 extends outside of the handle 234, and the mount 258 is inside the handle 234.

FIG. 7 illustrates the percutaneous cutting device 200 in an assembled, cross sectional view. As shown in FIG. 7, the spring 262 bears against an internal guide 268 and the mount 258 of the elongated cutter 248. The elongated cutter 248 extends only partially through the elongated cutter guide 246. The tab 260 extending from the handle 234 allows an operator to apply a distal force to the elongated cutter 248 and cause the elongated cutter 248 to move with respect to the elongated cutter guide 246 against the force of the spring 262. The cutting action of the elongated cutter 248 is described below with reference to FIGS. 8-9E.

Figure 8:
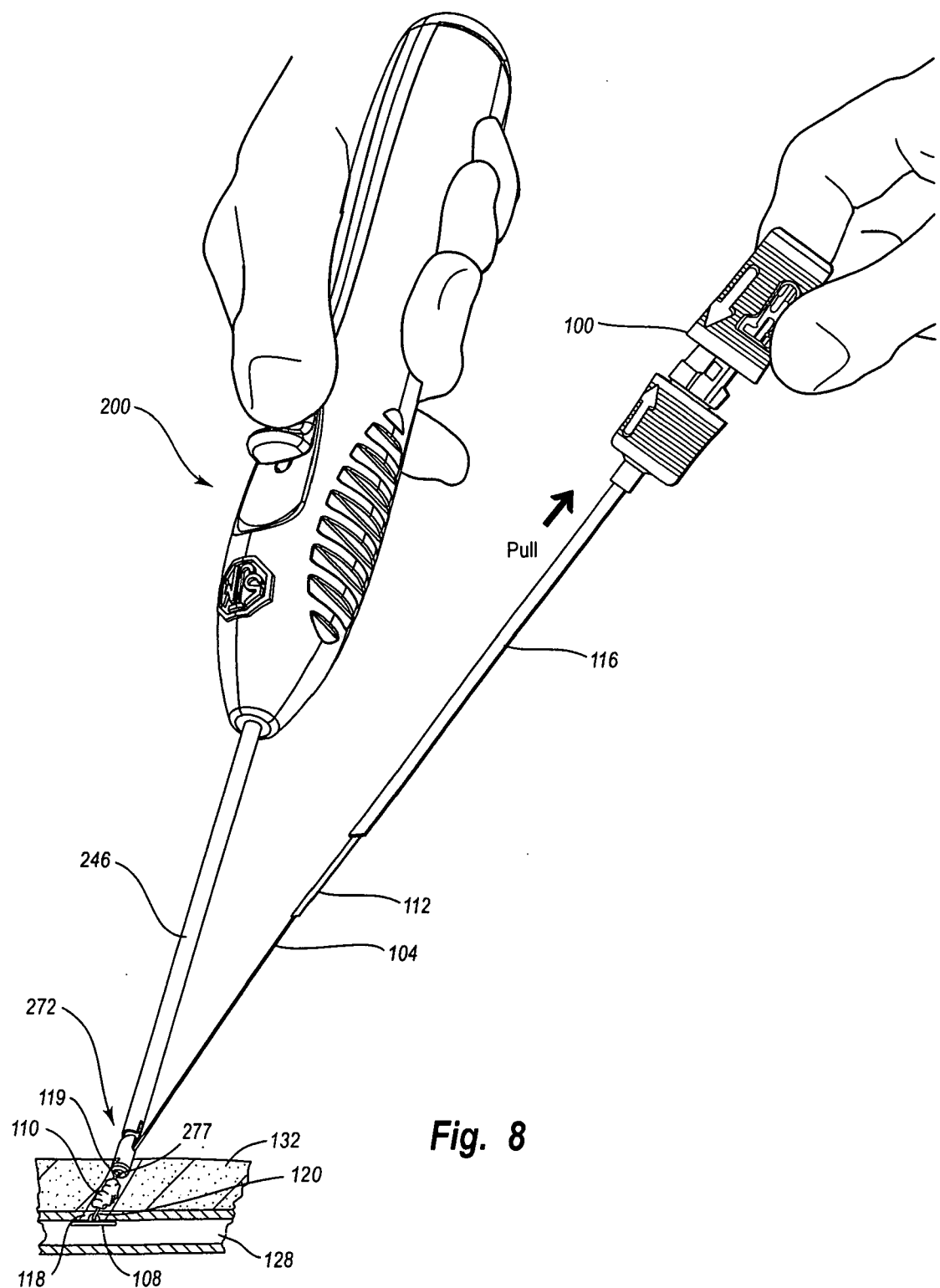
FIG. 8 is an assembled perspective view of the percutaneous filament cutting device of FIG. 6.
Figure 9B:
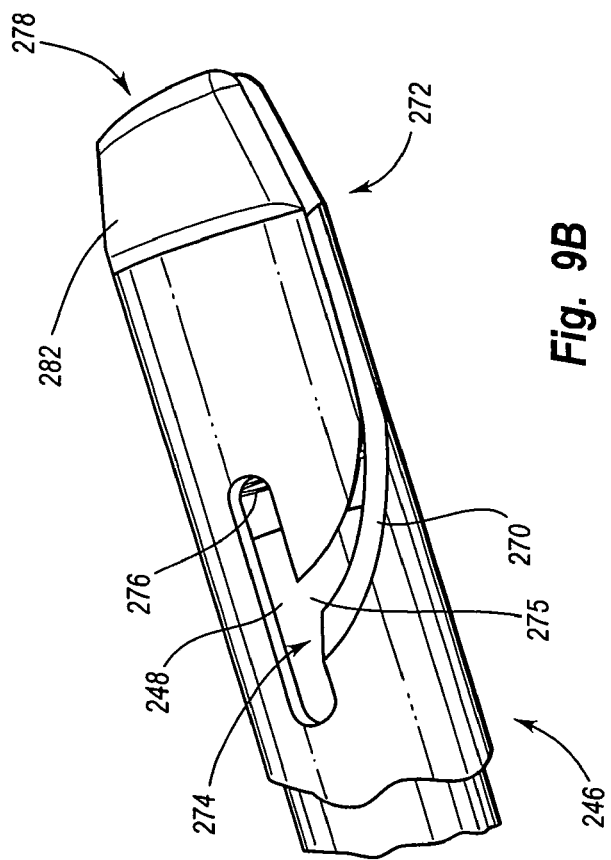
FIG. 9B is a blown up top view of the tip portion of the percutaneous filament cutting device of FIG. 6.
Figure 9D:
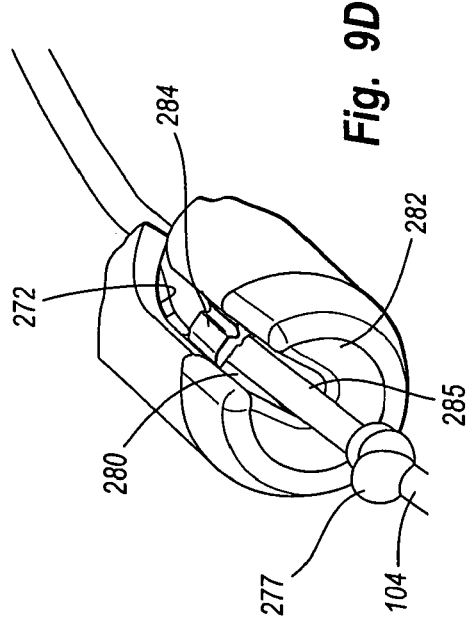
FIG. 9D is a blown up end perspective view of the tip portion of the percutaneous filament cutting device of FIG. 6 with a suture inserted therein.
Figure 9A:
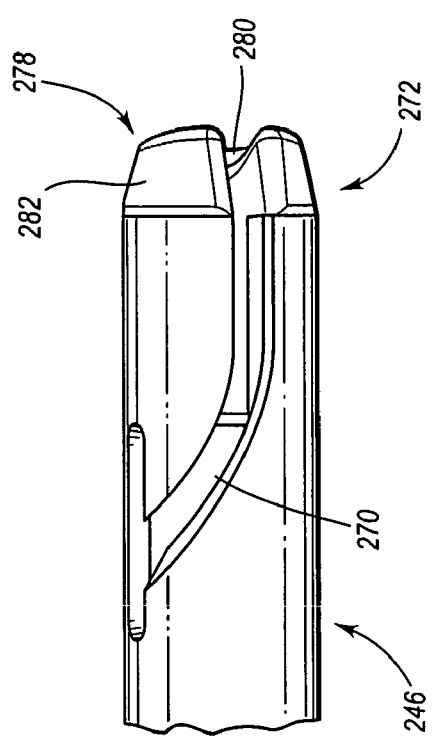
FIG. 9A is blown up side view of a tip portion of the percutaneous filament cutting device of FIG. 6.
Figure 9C:
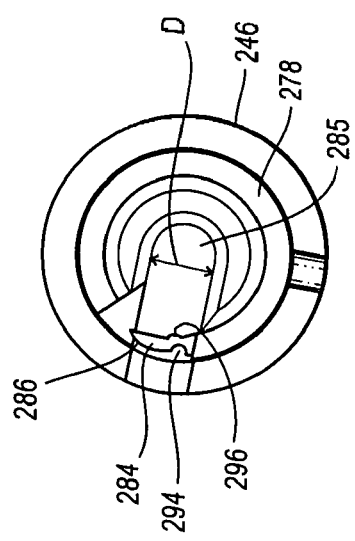
FIG. 9C is a blown up cross-sectional view of the tip portion of the percutaneous filament cutting device of FIG. 6.
Figure 9F:
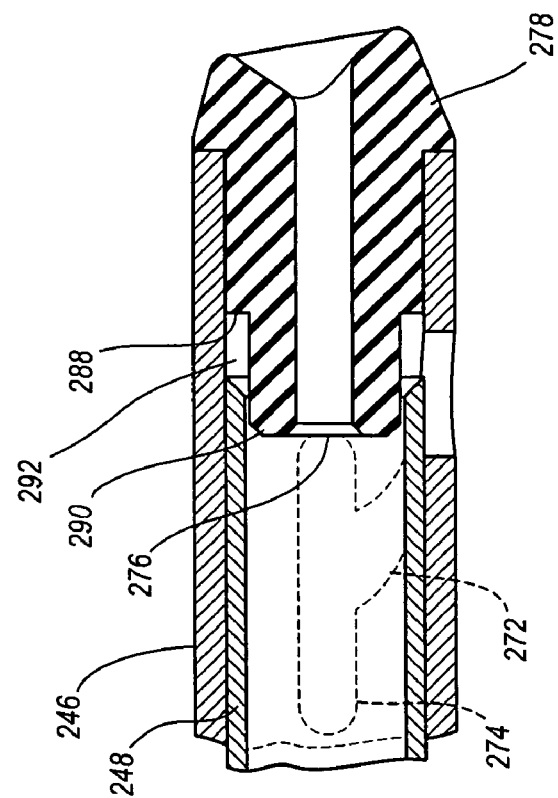
FIG. 9F is a blown up side view of the tip portion of the percutaneous filament cutting device of FIG. 6 with hidden lines illustrating internal hidden features.
Figure 9E:
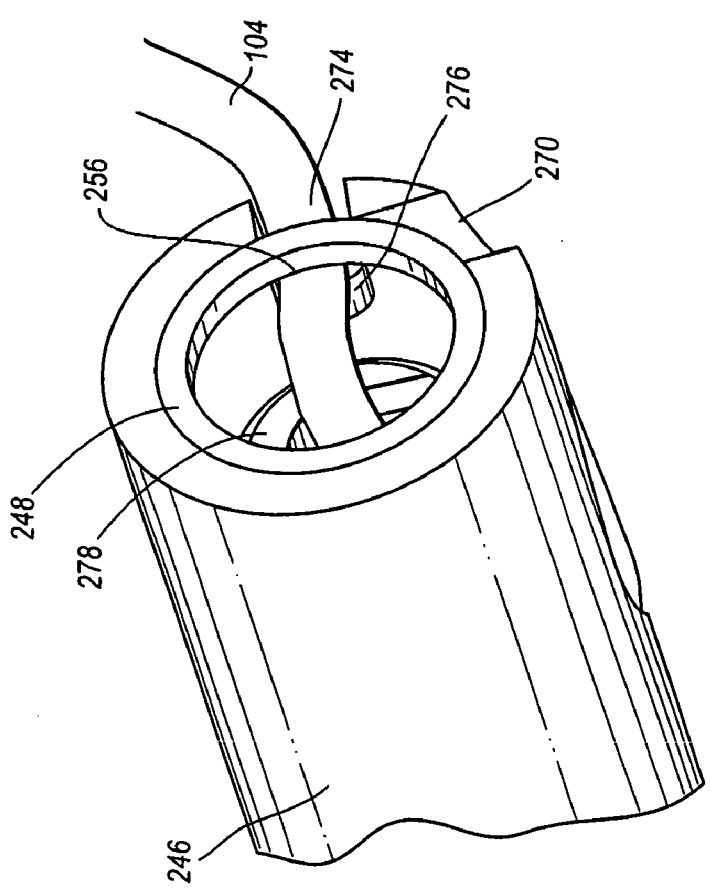
FIG. 9E is a reverse blown up end perspective view of the tip portion of the percutaneous filament cutting device of FIG. 6 with the suture being cut by a blade.

Referring to FIGS. 8-9E, a filament such as the suture 104 of the closure device 100 may be threaded into the percutaneous cutting device 200. The elongated cutter guide 246 includes a filament insertion slot such as a helical filament insertion slot 270 (FIG. 9A) shown at a first or distal end 272. The helical filament insertion slot 270 allows a filament to be threaded into the elongated cutter guide 246 at any point along the filament. The helical filament insertion slot 270 may extend for approximately 90° as shown in FIG. 9A, although the slot 270 may also traverse smaller or larger angles, such as 180°. The helical filament insertion slot 270 is open at the first end 272.

The helical filament insertion slot 272 also opens into a side of a longitudinal guide slot or cutting window 274 shown most clearly in FIG. 9B. The guide slot 274 is shaped generally like a capsule with an open area 275 in the side communicating with the helical filament insertion slot 272. The open area 275 may define an intersection point between guide slot 274 and the filament insertion slot 272. The guide slot 274 provides a geometry that generally prevents an inserted filament from falling out of the helical filament insertion slot 270. As a filament such as the suture 104 (FIGS. 8, 9E) is threaded into the helical filament insertion slot 270 and then into the guide slot 274, the suture 104 tends to fall toward a lower wall 276 of the guide slot 274 (also referred to as a termination point of the guide slot 274), which prevents the suture 104 from slipping back out of the helical filament insertion slot 270 at the open area 275.

The first end 272 of the elongated cutter guide 246 may attach to a tip such as a molded tip 278. The molded tip 278 also comprises a filament insertion slot 280 substantially aligned with the helical filament insertion slot 272. The molded tip 278 is preferable plastic and partially inserted into the elongated cutter guide 246 such that a tapered outer distal end 282 abuts and is flush with the elongated cutter guide 246 (FIG. 9A). The molded tip 278 also includes a radially inward taper surface 284 best seen in FIG. 9D that is concave and receptive of a filament. The radially inward taper surface 284 funnels or leads to a internal filament lumen 285 (FIGS. 9C-9D) defined by the molded tip 278 and/or the elongated cutter guide 246. Therefore, a filament may be threaded into the helical filament insertion slot 270 such that the filament extends into the internal filament lumen 286 and back out the guide slot 274. The internal filament lumen 285 of the molded tip 278 comprises a diameter or effective diameter (e.g. distance D of FIG. 9C) that is large enough to allow a filament to slide freely therethrough. However, the diameter or effective diameter of the internal filament lumen 285 through the molded tip 278 is small enough to prevent any knots tied in the filament, such as knot 277 (FIGS. 8 and 9D) from entering through the tip via the radially inward taper surface 284. Thus, knots such as knot 277 used to cinch and hold the sealing plug 110 (FIG. 3) cannot enter the elongated cutter guide 246 and be cut. Instead the knot 277 is pushed toward the sealing plug 110 by the molded tip 278. The diameter or effective diameter D of the internal filament lumen 285 may be no more than approximately two to three times an associated filament diameter. For example, for a suture with a diameter of 0.12 mm, the internal filament lumen 285 diameter may be no more than approximately 0.35 mm.

The filament insertion slot 270 and/or the tip insertion slot 280 may include a holding or caging feature to retain a filament once inserted. For example, as shown in FIGS. 9C-9D, the tip insertion slot 280 includes a one-way movable door such as a cantilevered arm 284 to cage the filament. The cantilevered arm 284 is movable radially inward from a first position shown, but not moveable radially outward from the first position. Therefore, in order to insert a filament through the filament insertion slot 270 and/or the tip insertion slot 280, the filament is pressed against the cantilevered arm 284, causing it to move radially inward from the first position and allowing the filament to pass through. When a force opening the cantilevered arm 284 is removed, the cantilevered arm returns to the first position. The cantilevered arm 284 may not move radially outward from the first position, as it abuts an interior wall 286. Therefore the filament is prevented from release without a concerted effort to press the cantilevered arm 284 inward while pulling the filament out. The cantilevered arm 284 may be compliant by including a detent 294 at the base of an outside surface of the arm 284, and a protrusion 296 at the base of an inside surface.

As shown in FIG. 9F, the molded tip necks down at a shoulder 288. A necked down section 290 thus forms an annulus 292 with the elongated cutter guide 246 that the elongated cutter 248 may pass into when actuated. The necked down section 290 preferably extends such that it is approximately coincident with the lower wall 276 of the guide slot 274. Therefore, when a filament such as a suture 104 is threaded through the percutaneous cutting device 200 as shown in FIG. 9E, the geometry between the necked down section 290 and the lower wall 276 of the guide slot 274 causes the suture to pass through the guide slot 274 at an angle of approximately 90° with respect to the elongated cutter guide 246 and the elongated cutter 248 when the elongated cutter 248 is actuated. In addition, the interior portion of the lower wall 276 may be sharpened to facilitate cutting by the blade end 256 of the elongated cutter 248 in a scissor-like manner. The necked down section 290 and the interior portion of the blade end 256 may be filleted to further facilitate a normal orientation of the suture 104 with respect to the elongated cutter 248.

Figure 10B:
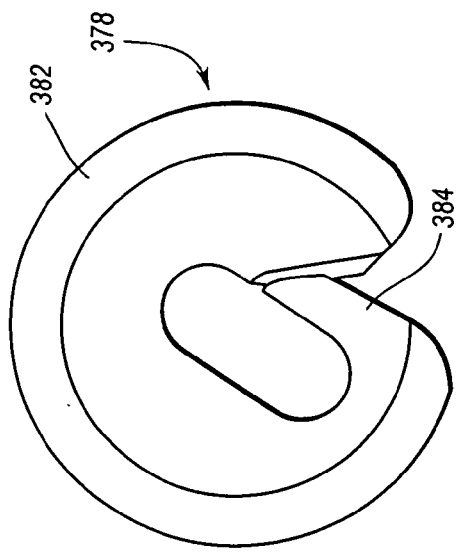
FIG. 10B is an end view of the tip portion of FIG. 10A with a one-way door in a first position.
Figure 10C:
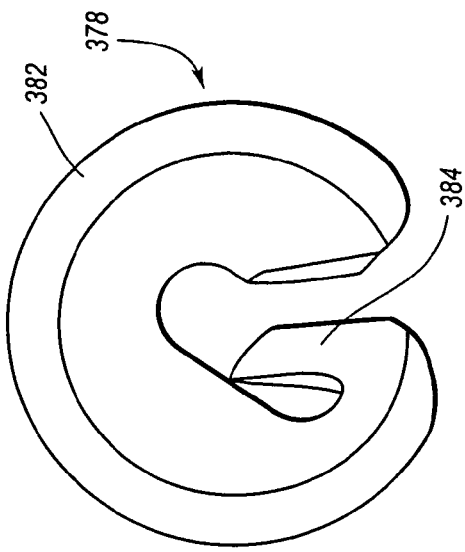
FIG. 10C is an end view of the tip portion of FIG. 10A with the one-way door in a second position.
Figure 10A:
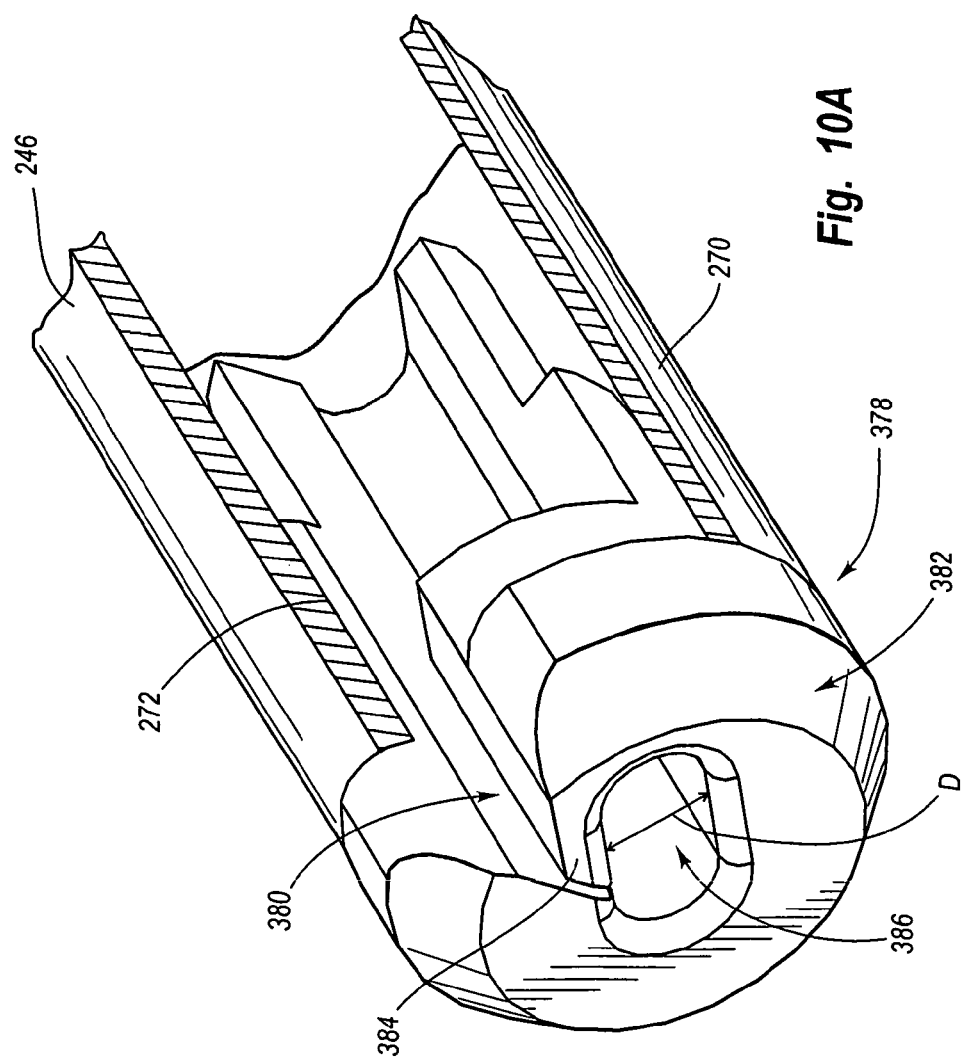
FIG. 10A is a blown up, perspective view of an alternative tip portion, shown partially in section, according to another embodiment of the present invention.

An alternative molded tip 378 is shown in FIG. 10A. According to the embodiment of FIG. 10A, the molded tip 378 does not include an interior taper. The molded tip 378 includes an exterior taper 382, but is otherwise similar to the molded tip 278 of FIGS. 9A-9E. Thus the molded tip 378 also comprises a filament insertion slot 380 substantially aligned with the helical filament insertion slot 272. The molded tip 378 is partially inserted into the elongated cutter guide 246 such that it abuts and is flush with the elongated cutter guide 246. An internal filament lumen 386 of the molded tip 378 may be shaped oblong as shown, circular, or some other shape. The internal filament lumen 386, however, comprises a diameter or effective diameter D that is large enough to allow a filament to slide freely therethrough but small enough to prevent any knots tied in the filament from entering. FIGS. 10B and 10C illustrate a one-way door 384 in closed, and open positions, respectfully, for allowing a filament into the insertion slot 380 (FIG. 10A) and subsequently caging the filament.

Operation of a tissue puncture closure system according to principles described above is as follows. The tissue puncture closure device 100 is inserted into the percutaneous incision 119. The anchor 108 is deployed and the closure device 100 is at least partially withdrawn from the incision. The tamping tube 112 (or other tamping device) is exposed and used to tamp the sealing plug 110 toward the anchor 108. Withdrawing the closure device 100 also exposes the suture 104 for cutting. The suture 104 is then threaded into the percutaneous cutting device 200 by pushing the filament past the cantileverd arm 284 of the filament insertion slot 270 and into the interior filament lumen 285. The percutaneous cutting device 200 is then urged toward the incision 119 and follows the filament path as the filament 104 enters the tip of the percutaneous cutting device 200 into the internal filament lumen 285. The percutaneous cutting device 200 is inserted into the incision 119 until at least the lower wall 276 of the guide slot 274 is subcutaneous. Advancement of the percutaneous cutting device 200 is limited by any knots in the suture 104, which may not pass into the internal filament lumen 285. When a desired percutaneous position is reached, the actuating tab 260 is depressed, which advances the elongated cutter 248 distally across the guide slot 274. The suture 104 is forced to exit the guide slot 274 at approximately a 90° angle by the geometry between the necked down portion 290 of the molded tip 278 and the blade end 254 of the elongated cutter 246. As the blade end 254 traverses the lower wall 276 of the guide slot 274, it cuts the suture 104 percutaneously, and the percutaneous cutting device 200 is removed from the incision 119.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:
1. A percutaneous filament cutting device, comprising:
   a housing;
   an elongated hollow cutter guide defining a lumen and attached to and extending from the housing, the elongated cutter guide comprising:
      a sidewall defining an outer surface of the elongated cutter guide;
      a filament insertion slot defined in the sidewall and extending directly and proximally from a distal end of the elongated cutter guide;
      a guide slot defined in the sidewall at a location proximal of the distal end of the elongated cutter guide, the guide slot intersecting the filament insertion slot at an intersection point, the guide slot including a termination portion extending distal of the intersection point;
   an elongated cutter slidingly disposed in the housing and extending partially through the elongated cutter guide.

2. A percutaneous cutting device according to claim 1, further comprising a biasing member disposed between the elongated cutter and the housing, the biasing member biasing the elongated cutter to a first position.

3. A percutaneous cutting device according to claim 1 wherein the elongated cutter comprises an actuator tab extending through a hole in the housing for operating the elongated cutter.

4. A percutaneous cutting device according to claim 1 wherein the elongated cutter comprises a blade end and an actuator end, the actuator end comprising a tab extending outside of the housing.

5. A percutaneous cutting device according to claim 1, wherein at least portions of the filament insertion slot extend in both a longitudinal direction and a lateral direction.

6. A percutaneous cutting device according to claim 1, wherein the filament insertion slot includes a helical shape and the guide slot is arranged longitudinally on the elongated cutter guide.

7. A percutaneous cutting device according to claim 1, wherein the intersection point of the filament insertion slot and the longitudinal guide slot forms an acute angle.

8. A percutaneous cutting device according to claim 1, further comprising:
   a one-way door movable radially inward but not movable radially outward for caging a filament positioned in the filament insertion slot.

9. A percutaneous cutting device according to claim 1, further comprising a molded tip having the filament insertion slot and a one-way movable door, the molded tip further comprising:
   a tapered outer distal end abutting and flush with the elongated cutter guide;
   a radially inward taper configured to receive a suture filament having a diameter and leading to the lumen;
   the lumen having a diameter no more than three times the diameter of the suture filament.

10. A percutaneous cutting device according to claim 1, further comprising a molded tip having the filament insertion slot and a one-way movable door, the molded tip further comprising:
   a tapered outer distal end abutting and flush with the elongated cutter guide;
   a radially inward taper leading to the lumen;
   wherein the lumen comprises a diameter no more than approximately 0.35 mm.

11. A percutaneous cutting device according to claim 1, further comprising:
   a one-way door movable radially inward but not movable radially outward for caging a filament positioned in the filament insertion slot;
   the one-way door comprising a cantilevered arm having a detent hinge.

12. A percutaneous cutting device according to claim 1 wherein the elongated cutter is coaxial with the elongated cutter guide.

13. A percutaneous cutting device according to claim 1 wherein the elongated cutter and the elongated cutter guide comprise hollow tubes.

14. A suture path tracking and cutting device, comprising:
a handle;
a hollow shaft of defining a lumen and extending from the handle, the shaft having a first open end at a distal end of the shaft and comprising a cutting window and a first suture insertion slot, the cutting window intersecting the first suture insertion slot at a intersection point, the first suture insertion slot extending directly and proximally from the first open end and the cutting window having a distal termination portion arranged distal of the intersection point and proximal of the first open end;
a cutting blade disposed in the shaft and biased to a first position;
a tip attached to the shaft at the first open end, the tip having a second suture insertion slot substantially aligned with the first suture insertion slot, the tip further comprising a one-way door for caging a suture.

15. A suture path tracking and cutting device according to claim 14 wherein the distal termination portion of the cutting window is configured to prevent inadvertent release of the suture from the cutting window to the first insertion slot.

16. A suture path tracking and cutting device according to claim 14 wherein the cutting window comprises a capsule shape that is arranged longitudinally and open at a side thereof to the first insertion slot.

17. A suture path tracking and cutting device according to claim 14 wherein the first suture insertion slot comprises a helical cut in the shaft.

18. A suture path tracking and cutting device according to claim 14 wherein the first suture insertion slot comprises a helical cut of up to about 180° in the shaft.

19. A suture path tracking and cutting device according to claim 14 wherein the one-way door comprises a cantilevered arm extending across the second insertion slot in a first position, the one-way door moveable radially inward from the first position but not radially outward from the first position.

20. A suture path tracking and cutting device according to claim 14 wherein the one-way door comprises a compliant arm having a base, an inside surface, an outside surface, a detent at the base of the outside surface, and a protrusion at the base of the inside surface.

21. A suture path tracking and cutting device according to claim 14 further comprising the suture and wherein an effective diameter of the lumen is no more than approximately three times the diameter of the suture.

22. A suture path tracking and cutting device according to claim 14 further comprising the suture and wherein the suture has a diameter, the lumen configured to receive the suture, but too small for any knots formed in the suture that have a maximum dimension greater than the diameter of the suture to pass therethrough.

23. A suture path tracking and cutting device according to claim 14 wherein the cutting blade is disposed in the shaft proximal of the cutting window in the first position, the cutting blade being movable distally at least partially across the cutting window in response to a force applied thereto.

24. A suture path tracking and cutting device according to claim 14, further comprising an actuator tab connected to the cutting blade for moving the cutting blade within the shaft, the actuator tab extending outside of the handle.

25. An internal tissue puncture closure and cutting system, comprising:
a closure device, the closure device comprising:
a filament extending from a first end of the closure device to a second end of the closure device;
an anchor for insertion through the tissue wall puncture attached to the filament at the second end of the closure device;
a sealing plug slidingly attached to the filament adjacent to the anchor;
a driving mechanism for tamping the sealing plug toward the second end;
a filament cutting device insertable percutaneously into an incision for cutting the filament below a skin level, the filament cutting device comprising:
an elongated hollow cutter guide defining a lumen and comprising:
a sidewall defining an outer surface of the elongated cutter guide;
a filament insertion slot defined in the sidewall and extending directly and proximally from a distal end of the elongated cutter guide;
a guide slot defined in the sidewall at a location proximal of the distal end of the elongated cutter guide, the guide slot intersecting the filament insertion slot at an intersection point, the guide slot including a termination portion extending distal of the intersection point;
an elongated cutter extending partially through the elongated cutter guide.

26. An internal tissue puncture closure system according to claim 25 wherein the filament cutting device further comprises a housing, the elongated cutter guide comprises a helical shape, and the guide slot is arranged longitudinally.

\* \* \* \* \*